United States Patent [19]

Wagner

[11] 4,185,088
[45] Jan. 22, 1980

[54] NON-ADHESIVE IONENE QUATERNARY POLYMER COMPOSITIONS USEFUL AS BILE ACID SEQUESTRANTS

[75] Inventor: Arthur F. Wagner, Princeton, N.J.

[73] Assignee: Merck & Co., Inc., Rahway, N.J.

[21] Appl. No.: 953,053

[22] Filed: Oct. 19, 1978

Related U.S. Application Data

[63] Continuation-in-part of Ser. No. 769,491, Feb. 17, 1977, abandoned.

[51] Int. Cl.$^2$ .............................................. A61K 31/74
[52] U.S. Cl. ........................................ 424/78; 424/329
[58] Field of Search .................................. 424/78, 329

[56] References Cited

U.S. PATENT DOCUMENTS 4,016,209   4/1977   Wagner et al. .............. 260/567.6 M

OTHER PUBLICATIONS

Chemical Abstracts 65:2071g (1966).
Chemical Abstracts 66:22211j (1967).

"Cab-O-Sil-Properties and Functions", Cabot Co., (8-1975).

Primary Examiner—Leonard Schenkman
Attorney, Agent, or Firm—Harry E. Westlake, Jr.; Rudolph J. Anderson, Jr.

[57] ABSTRACT

The invention disclosed herein relates to novel non-adhesive, free-flowing, pharmacologically acceptable compositions comprising ionene quaternary polymers effective as bile acid sequestrants, such as poly-[{methyl-(3-trimethylammoniopropyl)iminio}trimethylene dichloride], adsorbed on a pulverulent, solid aggregate of large surface to mass ratio, such as fumed silicas and silica aerogels. It also relates to the novel process for preparing such adsorbate compositions which comprises forming a substantially, uniform suspension of the finely-divided solid aggregate in an aqueous solution of poly-[{methyl-(3-trimethylammoniopropyl)iminio}-trimethylene dichloride], evaporatively removing the water from the suspension, and drying the adsorbate thus produced.

4 Claims, No Drawings

NON-ADHESIVE IONENE QUATERNARY POLYMER COMPOSITIONS USEFUL AS BILE ACID SEQUESTRANTS

CROSS-REFERENCE TO RELATED CASES

This is a continuation-in-part of co-pending application Ser. No. 769,491, filed Feb. 17, 1977 now abandoned.

DISCLOSURE OF THE INVENTION

Certain novel ionene polymers, and in particular poly-[{methyl-(3-trimethylammoniopropyl)-iminio}-trimethylene dichloride], are highly efficient as bile acid sequestrants. Poly-[{methyl-(3-trimethylammoniopropyl)iminio}trimethylene dichloride] is, however, extremely hygroscopic and when exposed to air, even at relatively low humidities, rapidly deliquesces to form initially a sticky, unworkable product, and finally a solution of the polymer. The polymer, which is stable at 11% relative humidity, liquifies on exposure to moist air of 23% relative humidity. This hygroscopic characteristic has presented a formidable problem in the handling and formulation of poly-[{methyl-(3-trimethylammoniopropyl)iminio}trimethylene dichloride] and, even when such formulation, e.g. by encapsulation or tableting, is conducted under anhydrous conditions, the resulting tablets and capsules rapidly absorb water under normal atmospheric conditions (the coatings of such capsules being permeable to water) to produce unsatisfactory adhesive, caking products.

Compositions comprising substantially uniform pulverulent mixtures of poly-[{methyl-(3-trimethylammoniopropyl)iminio}trimethylene dichloride] with various pharmacologically acceptable solid carriers, such as powdered silica, starch, talc, cellulose and kaolin, when prepared by thoroughly dry-mixing the components (as in a ball mill) under substantially anhydrous conditions, are adhesive in character, and ordinarily become sticky and caking after relatively short exposure to air at 23% relative humidity.

It is now discovered that substantially non-adhesive, powdered poly-[{methyl-(3-trimethylammoniopropyl)iminio}trimethylene dichloride] adsorbate compositions, which remain free-flowing and non-caking, even after prolonged contact with moist air of greater than 33% and in some instances, up to 76% relative humidity, are prepared by forming a substantially uniform suspension of a finely-divided, solid amorphous aggregate, preferably a fumed silicon dioxide or micron-sized silica aerogel, in an aqueous solution of poly-[{methyl-(3-trimethylammoniopropyl)iminio}trimethylene dichloride], evaporatively removing the water from the suspension, and drying the adsorbate composition thus produced.

Fumed silicon dioxides are prepared by burning silicon tetrachloride in a flame of hydrogen and oxygen to produce primary spherical paticles which, while still semi-molten, fuse into clusters of such particles called aggregates; these aggregates, during further cooling and collecting become physically entangled to form agglomerates. The latter, upon dispersion in an aqueous solution, can disentangle to reform aggregates. Fumed silicon dioxides so prepared are supplied in the form of light, fluffy, amorphous pure white, non-toxic, pharmacologically acceptable powders approved by FDA for use as a direct food additive, under the tradename Cab-O-Sil, by Cabot Corporation, 125 High Street, Boston, Mass. Similar non-toxic, FDA approved, amorphous micron-sized synthetic silicas are supplie under the tradename SYLOID silica aerogels and xerogels by W. R. Grace and Co., Davison Chemical Division, Charles and Baltimore Streets, Baltimore, Md. These aerogels and xerogels are prepared by the reaction of sulfuric acid and sodium silicate. The aerogels are highly porous solids formed by replacement of liquid in a gel by gas so that there is little shrinkage. The xerogels are porous solids formed from a gel by drying with unhindered shrinkage.

It is ordinarily preferred to employ approximately equal weights, on a dry basis, of fumed silicon dioxide or silica aerogel and poly-[{methyl-(3-trimethylammoniopropyl)iminio}trimethylene dichloride], although substantially non-adhesive adsorbate compositions are prepared utilizing a weight ratio of about 40 parts fumed silica to 60 parts polymer; fumed silica- or silica aerogel-polymer adsorbates containing up to 75% amorphous silica are likewise non-adhesive, and effective as bile acid sequestrants, but are not ordinarily employed because of their increased proportion of amorphous silica material.

The fumed silicas, silica aerogels and silica xerogels used in these compositions differ in physical properties such as unit surface area, pore volume, particle size and density, and certain of the 1:1 polymer adsorbates made therefrom differ in flow characteristics. The fumed silica-polymer adsorbates and silica aerogel-polymer adsorbates easily meet the criterion of being non-adhesive and free-flowing after prolonged exposure to moist air or relative humidity greater than 35% and are useful for pharmaceutical handling and formulation. The silica xerogel SYLOID 72-polymer adsorbate is the only one of the three silica xerogel-polymer adsorbates tested that is a potentially useful formulation.

The process of preparing these adsorbate compositions is ordinarily conducted by first forming a substantially uniform suspension of fumed silica or silica aerogel in approximately ten to fifty times its weight of water, and slowly adding to this suspension, with rapid stirring, a dilute (preferably about 10%) aqueous solution of poly-[{methyl-(3-trimethylammoniopropyl)iminio}trimethylene dichloride]. The rate of addition is ordinarily adjusted so as to be complete in about 5 to 15 minutes, and the resulting milky suspension is stirred vigorously for a short period of time, e.g. about 5 to 15 minutes. The suspension is then evaporated to dryness under reduced pressure, while stirring and maintaining the temperature within the range of about 25° C. to 40° C.; the temperature should not exceed 50° C. during this evaporation step, since some discoloration of the polymer can occur above this temperature. The residual powdered silica-polymer adsorbate composition is then dried in vacuo at a temperature of about 25° C. to 40° C., and may be milled.

It is a preferred feature of the present invention that it is not necessary to employ isolated solid polymer for preparing the dilute aqueous solution of poly-[{methyl-(3-trimethylammoniopropyl)iminio}trimethylene dichloride] employed in the above-noted procedure for preparing the fumed silica- or silica aerogel-polymer adsorbate composition. Instead, the aqueous polymerization reaction solution can itself be employed in this procedure, thereby avoiding the isolation, drying and storage of the highly-hygroscopic poly-[{methyl-(3-trimethylammoniopropyl)iminio}trimethylene dichloride]. This preferred method thus results in the direct production, from the aqueous polymerization reaction solution, of the desired poly-[{methyl-(3-trimethylammoniopropyl)iminio}trimethylene dichloride]-amorphous silica adsorbate composition in a non-adhesive form adapted for pharmaceutical formulation.

The superiority of these poly-[{methyl-(3-trimethylammoniopropyl)iminio}trimethylene dichloride]-amorphous silica adsorbate compositions over those compositions prepared by dry-mixing the components is demonstrated in the 1:1 fumed silica Cab-O-Sil M5-polymer formulations. The hygroscopicity of the adsorbate composition prepared by the aqueous method is appreciably greater than that of the composition prepared by dry-mixing and milling the components. It is indeed surprising that, in spite of its greater hygroscopicity, the presently invented fumed silica-poly-[{methyl-(3-trimethylammoniopropyl)iminio}trimethylene dichloride]-dsorbate composition remains completely non-adhesive, non-caking and free-flowing after two days exposure to moist air of 47% relative humidity, flows freely after a 24-hour exposure to moist air of 76% relative humidity, or exhibits only slight caking after exposure to moist air of 76% relative humidity for 48 hours, whereas the composition obtained by dry-mixing the same components became adhesive and caking even after a few hours exposure to moist air of 33% relative humidity.

Effective lowering of cholesterol blood levels is obtained by the oral administration of remarkably small dosages of the poly-[{methyl-(3-trimethylammoniopropyl)iminio}trimethylene dichloride]-fumed silica or poly-[{methyl-(3-trimethylammoniopropyl)iminio}-trimethylene dichloride]-silica aerogel adsorbate compositions of this invention. This enables a flexibility of formulation previously unavailable. These poly-[{methyl-(3-trimethylammoniopropyl)iminio}trimethylene dichloride]-amorphous silica compositions are light, fluffy, pulverulent powders, and are suitably used as such, or admixed with appropriate amounts of conventional pharmaceutically acceptable binders and/or additional solid carrier agents, such as starch, gelatin, sugars, such as glucose and lactose, methylcellulose, natural and synthetic, talc, synthetic gums, and the like. The compositions are preferably made into unit dosage forms such as tablets or filled gelatin capsules or, if desired, the premeasured dose may be enclosed in a foil or paper envelope which can be readily torn open and added to edible liquids such as fruit juices or other beverages. The unit dosage may also include supplementary vitamins and minerals. The unit dose composition may comprise from 10 to 99% by weight of the poly-[{methyl-(3-trimethylammoniopropyl)iminio}-trimethylene dichloride]-fumed silica or poly-[{methyl-(3-trimethylammoniopropyl)iminio}trimethylene dichloride]-silica aerogel adsorbate composition, the remainder being carriers, flavorings, excipients, flow agents and the like. In such unit dose, the active polymer may comprise from 100 milligrams to up to 10 grams in powder packets.

For convenience of administration, it is preferred to employ tablets or capsules containing 300–600 milligrams of adsorbate compositions comprising equal amounts of fumed silica or silica aerogel and poly-[{methyl-(3-trimethylammoniopropyl)iminio}trimethylene dichloride]. Such unit dosage compositions would thus provide about 150–300 milligrams of the bile acid sequestrant polymer, poly-[{methyl-(3-trimethylammoniopropyl)iminio}trimethylene dichloride]; a capsule or tablet containing 600 milligrams of adsorbent composition taken four times per day would thus provide a daily dosage of 1.2 grams of poly-[{methyl-(3-trimethylammoniopropyl)iminio}trimethylene dichloride]. Multiple dosages, e.g., two or three tablets or capsules can, of course, be taken at one time if desired. In the case of tablets, a plastic film can be applied, if desired, to seal the tablets from moisture, and to mask the taste of the poly-[{methyl-(3-trimethylammoniopropyl)iminio}trimethylene dichloride] in ways well known in the art. An enteric coating such as fats, fatty acids, waxes and mixtures thereof, shellac, ammoniated shellac, and cellulose acid phthalates, may also be applied by techniques well known and accepted.

The following examples illustrate methods of carrying out the present invention, but it is to be understood that these examples are given for purposes of illustration and not of limitation.

EXAMPLE 1

A mixture of 300 mg. of poly-[{methyl-(3-trimethylammoniopropyl)iminio}trimethylene dichloride] and 300 mg. of the fumed silica Cab-O-Sil M5 in 10 ml. of water prepared and transferred to a round-bottom flask. The mixture was concentrated on a rotary evaporator in vacuo at 45° C. and dried in vacuo for 1 hour at 45° C. This product remained free-flowing after exposure to moist air of 76% relative humidity for 24 hours. The exposed sample was then partially air dried by exposure to the atmosphere for 1 hour at ambient conditions before re-exposure to moist air of 76% relative humidity for a second 24-hour period. The sample remained free-flowing after the second 24-hour exposure at 76% relative humidity.

EXAMPLE 2

A mixture of about 40 grams of the fumed silicon dioxide Cab-O-Sil M5 and 1100 ml. of water was stirred vigorously until a thin, lump-free, substantially uniform suspension was obtained. This suspension was stirred while slowly adding thereto a solution of 40 grams of anhydrous poly-[{methyl-(3-trimethylammoniopropyl)iminio}trimethylene dichloride] in 300 ml. of water. The resulting suspension was evaporated to dryness under reduced pressure, and the residual adsorbate was dried in vacuo for a period of about 15 hours and milled to give about 85 grams of a white, fluffy, free-flowing, non-caking powder containing about 5% of adsorbed moisture. This adsorbate remained free-flowing and non-caking upon exposure for two days to moist air of 47% relative humidity and exhibited only slight caking on exposure to moist air of 76% relative humidity for 24 and 48 hours.

EXAMPLE 3

A mixture of 122.61 mg. of Packard Thixotropic Gel Powder (Packard Thixotropic Gel Powder is a form of the fumed silica Cab-O-Sil provided by Packard Instrument Company, Inc., 2200 Warrenville Road, Downers Grove, Ill. 60515) was suspended in 5 ml. of water using a high speed stirrer. A solution containing 121.1 mg. anhydrous weight of poly-[{methyl-(3-trimethylammoniopropyl)iminio}trimethylene dichloride] in 3 ml. of water was added slowly while agitation was continued. The resulting milky suspension was evaporated to dryness in vacuo, and the residual adsorbate was further dried in vacuo to give a fumed silica-poly-[{methyl-(3- trimethylammoniopropyl)iminio}-trimethylene dichloride] composition in the form of a fluffy, white, free-flowing, non-caking powdery adsorbate which, upon exposure to laboratory atmosphere (relative humidity approximately 35%) for a period of 15 hours, fully retained its free-flowing and non-caking characteristics.

EXAMPLE 4

A mixture of 1.34 g. of Packard Thixotropic Gel Powder was suspended in 60 ml. of water using a high speed stirrer. A solution containing 1.34 g. anhydrous weight of poly-[{methyl-(3-trimethylammoniopropyl)iminio}trimethylene dichloride] in 30 ml. of water was added slowly while agitation was continued. The resulting milky suspension was stirred vigorously for approximately one-half hour, and then evaporated to dryness in vacuo, and the residual adsorbate was further dried in vacuo to give approximately 2.5 g. of a fumed silica-poly-[{methyl-(3-trimethylammoniopropyl)iminio}-trimethylene dichloride] composition in the form of a fluffy, white, free-flowing, non-caking powdery adsorbate. This material remained free-flowing and non-caking after 24 hours exposure to air of 76% relative humidity.

EXAMPLE 5

A suspension of 1.00 g. of the silica aerogel SYLOID 244 in 10 ml. of water was stirred while a solution of 1.00 g. of poly-[{methyl-(3-trimethylammoniopropyl)iminio}trimethylene dichloride] in 6 ml. of water added. The resulting mixture was concentrated to dryness in vacuo and the product was dried in vacuo to yield material that remained free-flowing after exposure to moist air of 76% relative humidity for 48 hours.

EXAMPLE 6

A solution of 2.00 g. of poly-[{methyl-(3-trimethylammoniopropyl)iminio}trimethylene dichloride] in 10 ml. of water was added to a stirred suspension of 2.00 g. of the silica aerogel SYLOID 266 in 35 ml. of water. The mixture was concentrated to dryness under reduced pressure at about 50° C. The product was ground by mortar and pestle and dried in vacuo over phosphoric anhydride. The product remained free-flowing after exposure to moist air of 76% relative humidity for 48 hours.

EXAMPLE 7

The procedure described in Example 6 was repeated by adding an amount of poly-[{methyl-(3-trimethylammoniopropyl)iminio}trimethylene dichloride] in the form of a 20% aqueous solution to a stirred aqueous suspension of an equal amount of the fumed silica Cab-O-Sil HS5, MS7, PTG or EH5 or the silica xerogel SYLOID 72, 74 or 63. The flow properties of the different preparations is as follows:

The product containing Cab-O-Sil HS5 flowed freely after exposure to moist air of 47% relative humidity for 48 hours and showed slight caking after a 24-hour exposure to moist air of 76% relative humidity.

The product containing Cab-O-Sil EH5, that containing Cab-O-Sil MS7, and that containing Cab-O-Sil PTG flowed freely after exposure to moist air of 33% relative humidity for 48 hours, and exhibited only slight caking on exposure to moist air of 47% relative humidity for 48 hours. On exposure to moist air of 76% relative humidity, the products containing Cab-O-Sil MS7 and Cab-O-Sil PTG showed slight caking on exposure for 24 hours and caking after 48 hours. The product containing Cab-O-Sil EH5 exhibited caking on exposure to moist air of 76% relative humidity for 3 hours.

The product containing SYLOID 72 showed slight caking after 48 hours at 33% relative humidity, but flowed freely on exposure to moist air of 47% relative humidity for 48 hours. At 76% relative humidity, this product was slightly caked at 24 hours and caked at 48 hours.

The product containing SYLOID 74 showed slight caking on exposure to moist air of 33% relative humidity after 24 hours and caked at 47% relative humidity. The product containing SYLOID 63 liquified after exposure to moist air of 33% relative humidity for 3 hours.

The poly-[{methyl-(3-trimethylammoniopropyl)iminio}trimethylene dichloride], utilized as the bile acid sequestrant polymer component of the adsorbate compositions prepared as described in the foregoing examples, as well as other ionene quaternary polymers and pharmacologically acceptable salts which may also be used as the polymer component in such adsorbate compositions, may be synthesized in accordance with various procedures described in copending applications Ser. No. 570,910, filed Apr. 23, 1975, now U.S. Pat. No. 4,016,209, issued Apr. 5, 1977, and Ser. No. 462,263, filed Apr. 19, 1974, now abandoned.

The chemical structure of the polymer components, which are referred to in the instant specifications and claims as "ionene quaternary polymers" and in which the anion and terminal groupings can vary depending on the synthesis procedure employed, may be represented by the following formula:

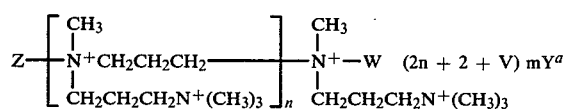

wherein n is the number of repeating units in the polymer; Y is a mono- or poly-valent, pharmacologically acceptable anion, a is the anionic charge on Y, and m is the reciprocal of a; W is propyl, hydroxypropyl, allyl, or an alkoxypropyl, such as ethoxypropyl or methoxypropyl; or W may be halopropyl, (such as chloropropyl, bromopropyl or iodopropyl) which is preferably converted, by reaction with ammonia, to a primary ammoniopropyl, or, by reaction with an amine, to a secondary, tertiary or quaternary ammoniopropyl grouping, for example, an alkylammoniopropyl, such as methylammoniopropyl, a dialkylammoniopropyl, such as dimethylammoniopropyl, or a trialkylammoniopropyl, such as trimethylammoniopropyl; and Z is allyl, N-trimethylammoniopropyl-N-methyl-3-aminopropyl, or N-trimethylammoniopropyl-N,N-dimethyl-3-ammoniopropyl; or Z may be halopropyl, (such as chloropropyl, bromopropyl or iodopropyl) which is preferably converted, by reaction with ammonia, to a primary ammoniopropyl, or, by reaction with an amine, to a secondary, tertiary or quaternary ammoniopropyl grouping, for example, an alkylammoniopropyl, such as methylammoniopropyl, a dialkylammoniopropyl, such a dimethylammoniopropyl, or a trialkylammoniopropyl, such as trimethylammoniopropyl; and V is the number of positively charged nitrogens (N+) in the W and Z groupings.

Various changes and modifications may be made in carrying out the present invention without departing from the spirit and scope thereof. Insofar as these changes and modifications are within the purview of the annexed claims, they are to be considered as part of this invention.

What is claimed is:

1. A bile acid sequestrant composition characterized as being non-adhesive and free-flowing after prolonged exposure to air at 35% relative humidity, which comprises a substantially uniform adsorbate of an ionene quaternary polymer on a fumed silica or silica aerogel, said polymer and silica having a weight:weight ratio of approximately 1:1, said ionene quaternary polymer having the following formula:

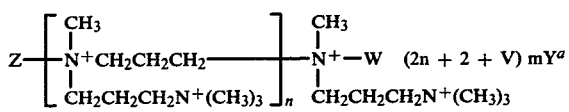

wherein n is the number of repeating units in the polymer; Y is a mono- or poly-valent, pharmacologically acceptable anion, a is the anionic charge on Y, and m is the reciprocal of a; W is propyl, hydroxypropyl, allyl, alkoxypropyl, halopropyl, ammoniopropyl, alkylammoniopropyl, dialkylammoniopropyl, or trialkylammoniopropyl; Z is allyl, N-trimethylammoniopropyl-N-methyl-3-aminopropyl, N-trimethylammoniopropyl-N,N-dimethyl-3-ammoniopropyl, halopropyl, ammoniopropyl, alkylammoniopropyl, dialkylammoniopropyl or trialkylammoniopropyl; and V is the number of positively charged nitrogens (N+) in the W and Z groupings, which is produced by the process which comprises forming a substantially uniform suspension of a fumed silica or silica aerogel in an aqueous solution of said ionene quaternary polymer, evaporatively removing water from this suspension, and drying the adsorbate thus produced.

2. The bile acid sequestrant composition of claim 1, wherein said ionene is poly-[{methyl-(3-trimethylammoniopropyl)iminio}trimethylene dichloride}.

3. A non-adhesive, free-flowing, pharmacologically-acceptable bile acid sequestrant adsorbate composition comprising approximately equal weights of poly-[{methyl-(3-trimethylammoniopropyl)iminio}trimethylene dichloride] and a fumed silica or silica aerogel produced by the process which comprises forming a substantially uniform suspension of a fumed silica or silica aerogel in approximately 10 to 50 times its weight of water, slowly adding to this suspension, with rapid stirring, a dilute aqueous solution of poly-[{methyl-(3-trimethylammoniopropyl)iminio}trimethylene dichloride], and evaporating the water from the resulting suspension under reduced pressure, while stirring and maintaining the temperature of the mixture at about 25°–40° C. and drying the adsorbate thus produced.

4. A unit dosage composition characterized as being non-adhesive and free-flowing after a few hours exposure to air at 35% relative humidity which comprises a tablet or capsule of about 150–300 milligrams of poly-[{methyl-(3-trimethylammoniopropyl)iminio}trimethylene dichloride] adsorbed onto an approximately equal weight of a fumed silica or silica aerogel produced by the process which comprises forming a substantially uniform suspension of a fumed silica or silica aerogel in an aqueous solution of poly-[{methyl-(3-trimethylammoniopropyl)iminio}trimethylene dichloride], evaporatively removing water from this suspension, and drying the adsorbate thus produced.

* * * * *